(12) United States Patent
Mazzone et al.

(10) Patent No.: US 10,953,178 B2
(45) Date of Patent: Mar. 23, 2021

(54) FILLED HOLLOW STRUCTURE AND TOOL FOR MANUFACTURING SAME

(71) Applicant: ResMed Limited, Bella Vista (AU)

(72) Inventors: Damien Julian Mazzone, Sydney (AU); Grant Moiler, Sydney (AU); Fiona Catherine Carroll, Hawkesbury (AU)

(73) Assignee: ResMed Pty Ltd, Bella Vista (AU)

( * ) Notice: Subject to any disclaimer, the term of this patent is extended or adjusted under 35 U.S.C. 154(b) by 600 days.

(21) Appl. No.: 15/695,288

(22) Filed: Sep. 5, 2017

(65) Prior Publication Data

US 2017/0361047 A1  Dec. 21, 2017

Related U.S. Application Data

(62) Division of application No. 13/705,787, filed on Dec. 5, 2012, now Pat. No. 9,782,554.

(60) Provisional application No. 61/566,850, filed on Dec. 5, 2011.

(51) Int. Cl.
| | |
|---|---|
| *A61M 16/06* | (2006.01) |
| *B29C 45/16* | (2006.01) |
| *B29L 31/00* | (2006.01) |
| *B29L 24/00* | (2006.01) |

(52) U.S. Cl.
CPC ........ *A61M 16/06* (2013.01); *A61M 16/0633* (2014.02); *B29C 45/1615* (2013.01); *B29C 45/1671* (2013.01); *A61M 2205/0216* (2013.01); *A61M 2205/0238* (2013.01); *A61M 2207/00* (2013.01); *A61M 2207/10* (2013.01); *B29L 2024/00* (2013.01); *B29L 2031/753* (2013.01)

(58) Field of Classification Search
CPC .. A61M 16/00; A61M 16/06; A61M 16/0605; A61M 16/0611; A61M 16/0616; A61M 16/0622; A61M 16/0627; A61M 16/0633; A61M 16/0666; A61M 2016/0661; A61M 2205/0216; A61M 2207/10; A61M 2210/0618; A61M 2210/0625; A61M 2210/1025; A61M 2207/00
See application file for complete search history.

(56) References Cited

U.S. PATENT DOCUMENTS

| | | | |
|---|---|---|---|
| 6,397,847 B1 * | 6/2002 | Scarberry | A61M 16/06 128/206.14 |
| 7,393,488 B2 | 7/2008 | Grose | |
| 2003/0196656 A1 * | 10/2003 | Moore | A61M 16/0622 128/201.22 |
| 2006/0096598 A1 * | 5/2006 | Ho | A61M 16/0683 128/206.24 |

(Continued)

FOREIGN PATENT DOCUMENTS

| | | |
|---|---|---|
| WO | WO 2008/089799 | 7/2008 |
| WO | WO 2009/062265 A1 | 5/2009 |

(Continued)

*Primary Examiner* — Colin W Stuart
(74) *Attorney, Agent, or Firm* — Nixon & Vanderhye P.C.

(57) ABSTRACT

A filled hollow structure includes an open hollow structure from a first material. The open hollow structure is at least partially closed by a closing structure. The hollow structure is filled with a filler medium. The filled hollow structure is overmoulded with a second material.

17 Claims, 13 Drawing Sheets

(56) References Cited

U.S. PATENT DOCUMENTS

| | | | |
|---|---|---|---|
| 2007/0221227 A1* | 9/2007 | Ho | A61M 16/0633 128/206.24 |
| 2010/0101581 A1* | 4/2010 | Lang | B29C 65/7847 128/205.25 |
| 2010/0294281 A1* | 11/2010 | Ho | A61M 16/0638 128/206.24 |
| 2013/0139824 A1 | 6/2013 | Mazzone et al. | |

FOREIGN PATENT DOCUMENTS

| | | |
|---|---|---|
| WO | WO 2009/143586 A1 | 12/2009 |
| WO | WO 2010/009877 | 1/2010 |

\* cited by examiner

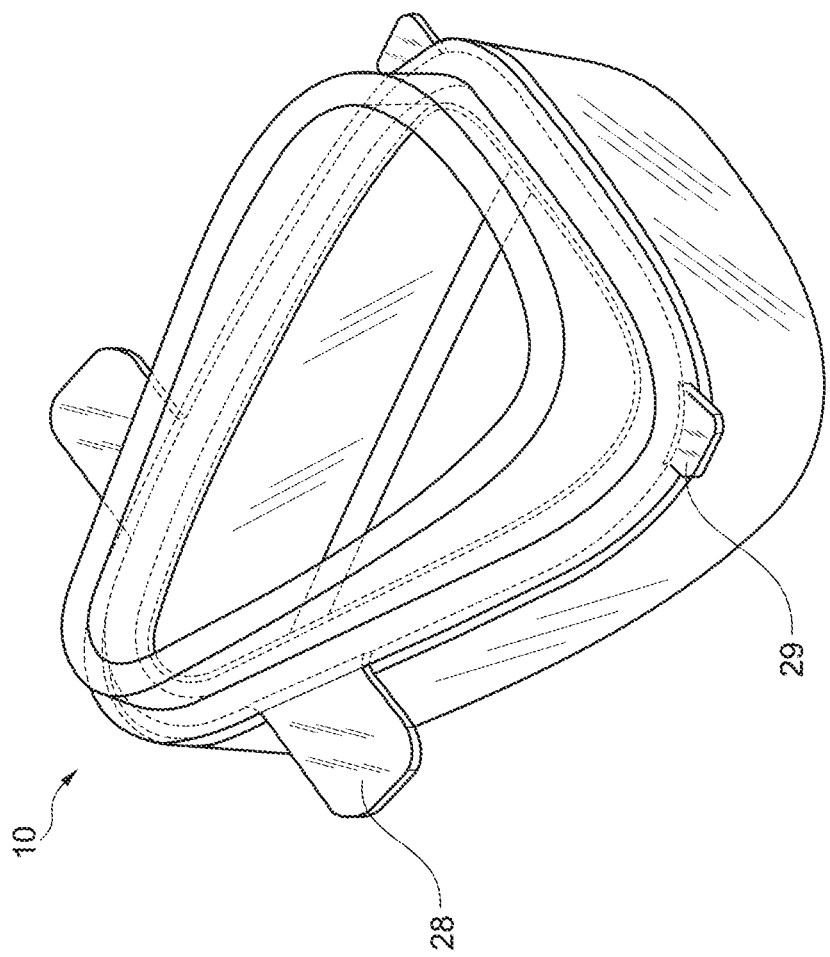

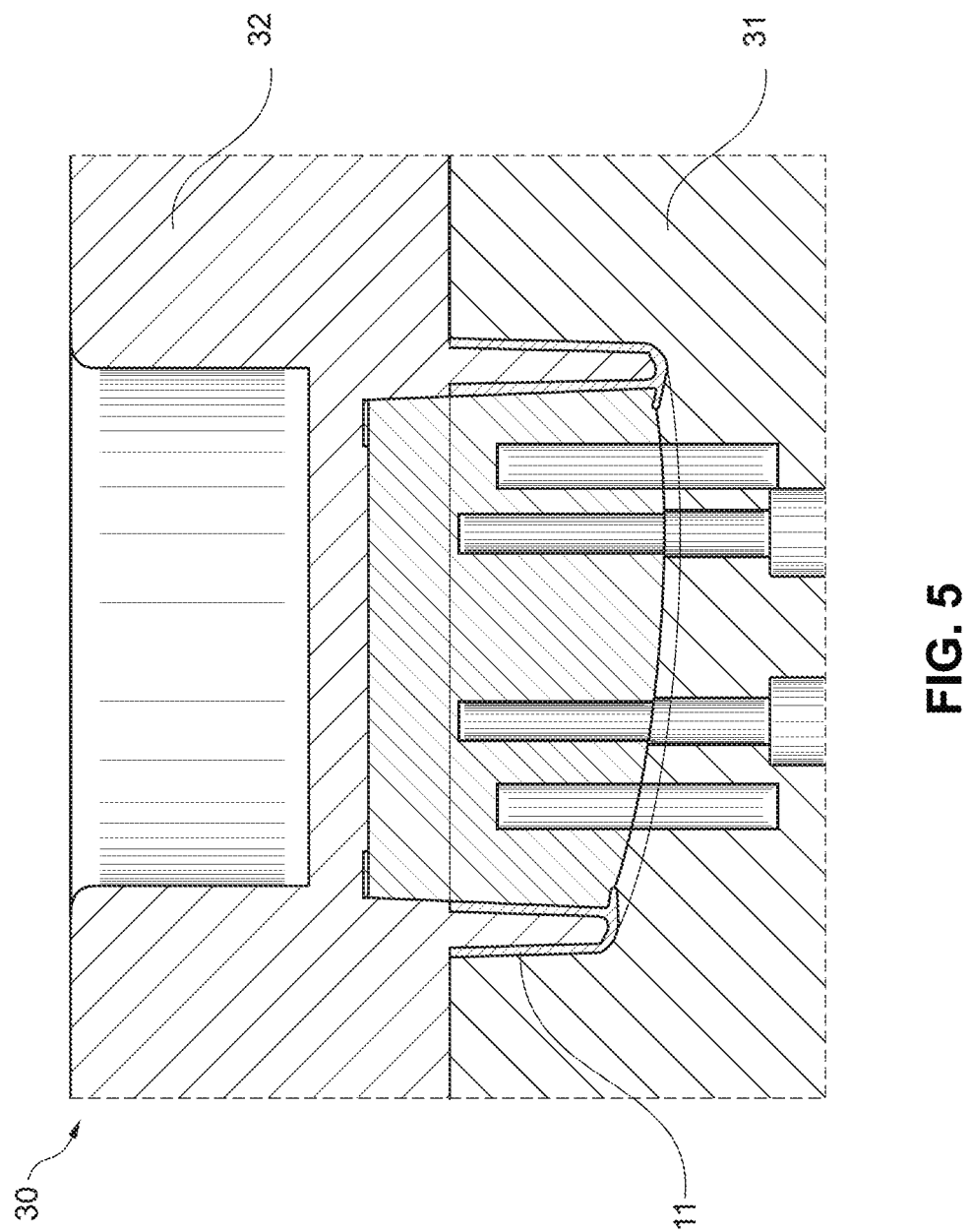

US 10,953,178 B2

FILLED HOLLOW STRUCTURE AND TOOL FOR MANUFACTURING SAME

CROSS REFERENCE TO RELATED APPLICATIONS

This application is a divisional of U.S. application Ser. No. 13/705,787, filed Dec. 5, 2012, which claims the benefit of U.S. Provisional Application No. 61/566,850 filed Dec. 5, 2011, the entire contents of each of which are hereby incorporated by reference in their entirety.

FIELD OF THE INVENTION

The invention relates to a method for producing a filled hollow structure and more particularly to a method for producing a closed, and filled hollow structure with a complex geometry. Furthermore, the present invention relates to a filled hollow structure and more particularly to a closed, and filled hollow structure obtainable by a method according to the present invention as well as to a tool for producing such filled hollow structure and/or to using said tool for performing a respective method.

BACKGROUND OF THE INVENTION

Hollow structures are known in the prior art, for example, in the field of face masks for delivering breathable gas or fluid to a patient. In such face masks, hollow cushions are used for providing contact zones for contacting the face of the user in order to improve comfort by moderating or otherwise distributing contact force. Furthermore, such structures are used as a sealing structure for sealing the mask interior from the exterior in the contact region where the mask rests on a user's face.

A disadvantage of hollow structures known in the art is that they are complicated to manufacture and numerous manual manufacturing steps are often necessary. Moreover, such hollow structures are either not closed, i.e., open, or are closed in an ineffective and/or complicated manner.

In particular, it is known to fill a mask cushion with silicone or gel wherein the hollow structure is closed by use of a silicone adhesive.

The solutions known in the prior art are in particular, not easy to handle, not durable, complicated and expensive to manufacture, not suitable for automating, not bio-compatible as well as optically and hygienically objectionable.

WO 2008/089799 discloses an improved method for producing a filled hollow structure by producing an open hollow structure of a first material, positioning the open hollow structure on a tool adapted to hold the open hollow structure, filling the open hollow structure with a filler medium, and then closing the filled open hollow structure with a second material.

SUMMARY OF THE INVENTION

One aspect of the present technology relates to a method for producing or manufacturing a filled hollow structure and particularly a filled hollow structure which overcomes the deficiencies of the prior art. More particularly, an aspect of the present technology relates to a method for manufacturing the filled hollow structure which is easy and efficient to carry out, which can be automated, and which provides for a durable as well as an optically and hygienically improved hollow structure. Moreover, an aspect of the present technology relates to a tool for producing a hollow structure as well as to an improved hollow structure.

Another aspect of the present technology relates to a method for producing a filled hollow structure, comprising the production or moulding of an open hollow structure or bladder of a first material (e.g., a structure having an opening) the structure having a hollow or a hollow area such as a pocket or a cavity, wherein at least a portion of the hollow is open towards the outside of the structure; providing a closing structure to at least partially close the open hollow structure; filling the hollow structure, with a filler medium; and overmoulding the filled hollow structure with a second material. Preferably, filling of the hollow structure may be at least partial.

Another aspect of the present technology is that it simplifies and or makes practical the filling of a complex cushion shape, for example a cushion geometry with a non-planar cushion-to-frame side.

According to the present technology a filler medium is preferably considered to be a medium being non-releasably contained in a structure, i.e. a medium which is to stay in a structure, such as a hollow structure. According to the present technology a filled hollow structure once overmoulded is preferably considered to non-releasably contain the filler medium.

According to the present technology a closing structure may be an inlay, a cap, a plug or the like that at least partially, mostly or entirely closes the open hollow structure, preferably in the area of the structure's opening. Preferably, provision of the closing structure closes the open hollow structure while maintaining the hollow or cavity. The hollow or cavity is then, preferably, filled with a gaseous medium such as gas or fluid. Therefore, providing a closing structure may comprise inserting a plug or an inlay into, preferably the opening of, the open hollow structure. The plug may fit snugly into the opening of the open hollow structure. In an embodiment of the present technology the plug may be preformed. However, alternatively or additionally, a plug may also be moulded onto and/or into the open hollow structure. In this context, it is to be noted that a closing structure as referred to in the present application is preferably a comparatively stiff or rigid element while not being limited thereto but may also or alternatively be at least partly elastic, pliable and/or flexible or the like.

According to the present technology the hollow structure may be filled after closing the open hollow structure with the closing structure. This is, the open hollow structure may be first closed and/or sealed with the closing structure, as discussed above, and subsequently at least partially filled with a filler medium. Therefore the closing structure provides at least one filling structure for filling the open hollow structure with the filler medium and/or at least one gas or fluid evacuation structure. Such structures may be closed but openable, such as piercable by means of gas or fluid pressure and/or a filling needle. In preferred embodiments of the technology, the hollow structure, therefore, may be filled through a hard or relatively hard closing structure that will not deform under the pressure or force from the filling material. Alternatively or additionally, the closing structure may be provided with at least one opening or hole for filling the open hollow structure with the filler medium and/or at least one opening or hole for gas or fluid evacuation. The closing structure may be a plug.

According to the present technology the hollow structure may be completely or partially filled with the filler medium. For example, in one form the filler medium may be injected.

In an additional step, a vacuum may be applied to the hollow before the filler medium is inserted into the hollow. The application of the vacuum to the hollow sucks gas or fluid out of the hollow before the filler medium is inserted into the hollow so that an improved, e.g., void free, filling of the hollow may be achieved. The application of vacuum and the filling may be carried out subsequently and/or simultaneously. The application of a vacuum may be advantageous in case, e.g., a viscous gel is used as a filler medium. In a further additional step, a vacuum may be applied to the hollow and the filler medium after the open hollow structure has been filled with the filler medium. This step may improve the optical and hygienically appearance of the filled hollow structure as well as its mechanical properties by reducing or eliminating voids occurring in the filler medium and by providing a desired shape or structure to the hollow structure. The hollow structure may comprise a connection adapted to allow pressure or a vacuum to be applied to the hollow structure. The connection may allow the vacuum to shape the structure and to fix the respective shape. In an embodiment, the connection may be closed or be adapted as a one way valve so that the vacuum may be maintained inside the hollow structure. The closing structure may be embodied as a connections structure.

According to the present technology the hollow structure may be overmoulded after closing the open hollow structure with a closing structure and filling the hollow structure with a filler medium. The closing structure may be adapted to substantially or completely inhibit contact between a second material used for overmoulding the closed and filled hollow structure and the filler medium and/or to separate or space apart such second material and the filler medium when the filled hollow structure is overmoulded. The filling structure, such as membrane, opening and/or hole of the closing structure may be closed by additional material and/or additional structures for this purpose and/or be designed to avoid contact of the filler medium and the second material.

The open hollow structure may be made of a flexible first material, e.g., a plastic or synthetic material such as an elastomer material or a material comprising elastomer components. For example, the first material used to produce the open hollow structure may be silicone such as liquid silicone rubber (LSR), or thermoplastic elastomer (TPE). In an embodiment, an open hollow structure may be an injection moulded plastic skin, e.g., made of silicone or a liquid silicone rubber (LSR).

In an embodiment, the hollow structure may include a first portion to be filled by filler medium, a second portion which is constructed to incorporate the closing structure and a third portion which is adapted for being overmoulded with the second material. Alternatively, the third portion may be optional and the hollow structure may comprise only the first and the second portions while the second portion comprises a sealing area that is adapted to form a seal along the perimeter of the inner and outer walls of the open hollow structure with the closing structure when said closing structure is inserted and/or overmoulded.

Furthermore, the hollow structure may have the general shape of a bladder and may include thin or skin-like outer walls which may have, according to embodiments, a differing wall thickness and/or topography. According to an embodiment, the open hollow structure may be described as having a tube-like structure bent to form a hollow structure having an inner wall and an outer wall which merge at one end of the structure via a bottom or transition wall and which is open at the other end of the structure. However, it is to be understood that the tube-like basic form as referred to above is not restricted to one diameter or a circular form but may comprise different cross sections, diameters, wall thicknesses, etc. The tube like structure may have been given a substantially triangular shape when seen from the top and/or the bottom. In an embodiment, when used in the field of face masks for delivering breathable gas or fluid to a patient, the hollow structure may have a generally tubular ring-like form with a generally triangular cross-section, particularly at its bottom or transition wall serving as a contact zone for resting on a patient's face. In an embodiment, when used in the field of face masks for delivering breathable gas or fluid to a patient, the wall thickness may vary and may lie in the range of about 0.1 mm to about 7 mm. In an embodiment, the hardness of the hollow structure may lie in the range from about 1 to 80 Shore A, e.g., about 20 to 60 Shore A or in the range of about 3 to 10 Shore A or about 5 Shore A or 40 Shore A. The hardness may depend on the spring and damping properties of the material and the ability to be easily demoulded.

According to the present technology the closing structure may be formed of a material suitable to snugly close and/or sealingly engage with the open hollow structure, e.g., of silicone. In embodiments, there could be a mechanical or chemical bond between the closing structure and the hollow structure.

The filler medium which is filled into the open hollow structure may include a fluid, i.e., a gaseous, dispersible and/or liquid fluid, an expandable fluid, foam, a powder and/or gel, preferably of silicone, oil, high viscosity fluids, wax, and/or low hardness elastomers. According to embodiments, a mixture of the above media may be used, e.g., two gels of different hardness or viscosity.

The second material may be a material suitable for overmoulding the filled hollow structure, preferably, a material suitable for overmoulding the closed and filled hollow structure. This again may be a flexible first material, e.g., a plastic or synthetic material such as an elastomer material or a material comprising elastomer components. Preferably the material is mouldable. For example, the second material used to overmould the filled hollow structure may be silicone, LSR, or TPE, TPU, TPV or comprise any of these materials. The second material may be provided as a gel or foam. In an embodiment, the second material may be or include the same material as the first material but different materials may also be provided. In particular, differing hardness of otherwise similar materials may me used as first and second materials. If completely dissimilar materials are used, they preferably are chosen such that they adhere to or are compatible with one another. The filled hollow structure may be overmoulded by injection moulding.

The closing structure may have a hardness that is higher than the hardness of the first and/or the hardness of the second material. In preferred embodiments of the technology the hollow structure, therefore, may be filled through a hard or relatively hard closing structure that will not deform under the pressure or force from the filling material. Materials having desired properties are, inter alia, disclosed in WO 2009/062265 A1 and WO 2009/143586 A1, which are hereby incorporated by reference in their entirety.

According to the present technology the filled hollow structure may be produced by multi-component injection moulding. The open hollow structure may be produced or moulded in a cavity of a moulding tool and may remain in a mould half thereof when being closed and/or when being filled and/or when being overmoulded. In an embodiment, the hollow structure is moulded, closed, filled and overmoulded while remaining in a mould half of a moulding tool. The tool may be a multi-component injection moulding tool.

According to the present technology any portion of a mould that forms a mould together with an additional mould portion is considered a "mould half". Therefore, a mould according to the technology may comprise several, e.g., more than two mould halves and preferably comprises three mould halves. When three mould halves are provided, a first mould half may form a first suitable moulding cavity when combined with a second mould half. A second suitable moulding cavity that is different from the first moulding cavity may be formed when the first mould half is combined with a third mould half. A mould "half" may, thus, also be denominated a mould "portion" in the context of the present technology. Alternatively there may be three or more mould halves which together form a moulding cavity.

In an embodiment, the open hollow structure may be held in the tool by the provision of a firm fit by the application of compressed gas or fluid and/or vacuum. Parts can also be held in a tool by specific retention features, or simply by the geometry of the tooling cores and parting lines. Also, the closed hollow structure may be removed from the tool by the use of compressed gas or fluid and/or vacuum and/or ejection pins.

In a further embodiment, the method according to the technology may include coating the hollow structure particularly in order to improve durability and/or optical and/or hygienically properties.

According to the present technology the filler medium may be structured to harden and/or soften if certain predetermined conditions are met. In an embodiment, the filler medium may harden and/or soften upon a trigger signal, such as a filling signal, or upon the application of heat or cold, etc. The filler medium may fill the open hollow structure quicker when softened and be more consistent.

It has been established that heating the tool used for moulding the open hollow structure and/or holding the hollow structure during filling, e.g. to about 130° C., may make it quicker to fill the hollow structure or bladder. Generally, and without wanting to be bound by a particular theory, the speed at which the filler material enters the hollow structure dictates the speed at which gas or fluid will exit the hollow. Thus, when the filler material enters the cavity fast enough, the the gas or fluid will evacuate the bladder quickly, which will positively influence the consistency of the fill.

However, if the filler goes into the bladder too quickly, the gases can become trapped in the filler as bubbles and lead to an uneven fill. Preferably balance between evacuating the gas and trapping gas bubbles is achieved. The evacuation structure (e.g. the opening for gas or fluid evacuation) may be sized to regulate the speed at which the gas is evacuated.

According to the present technology the filler medium may be at least partially cured. In an embodiment, the filler medium is cured in the mould used for producing the open hollow structure. Such curing may involve, depending on the conditions and the materials used, e.g., the addition or removal of energy, application of temperature, i.e., heat or cold, radiation, e.g., UV-light, the addition of further substances and/or time factors, i.e., waiting time, etc., foaming, and/or initiation of crystallization.

The walls of the open hollow structure may act as an insulating layer to prevent the filler medium from curing in a hot tool to quickly, e.g. before the filler medium, such as a gel, has sufficiently spread through the bladder.

According to the present technology the method may further include providing a support structure between the filler medium and the second material. The support structure may also be provided between the closing structure and the second material used for overmoulding the filled hollow structure. The support structure may be formed as a separate element or integrally with the closing structure and may be at least partially, substantially or entirely overmoulded when overmoulding the filled hollow structure with the second material.

In an embodiment, the support structure may substantially inhibit contact between the second material and the filler medium. For this purpose the support structure may cooperate with the closing structure. For example, the support structure may substantially obstruct at least one opening and/or hole provided in the closing structure. Preferably, the support structure covers the closing structure and/or prevents the second material from encroaching on the filler medium.

According to an embodiment, the support structure may be a plastic support member. Preferably, the support structure is relatively rigid or rigid. The material used for the support structure is preferably harder than the first material, the second material and/or the material used for the closing structure.

According to an embodiment, the support structure may include a connection structure adapted to connect the filled hollow structure to further structures. For example, according to an embodiment, the filled hollow structure may form part of a breathing mask and thus may be suitable to be connected with other structures, to fulfill other or additional functions, and/or to form additionally other structures such a mask and/or in order to form a mask assembly including means for attaching such a mask to a patient's face. According to the present technology the filled hollow structure may be a cushion for a breathing mask, particularly for providing a tight and comfortable contact between the mask and a user. The connection structure may be adapted to connect the hollow structure to the frame of the breathing mask and/or to a means for attaching the mask to the patient's face, e.g., a headgear. Alternatively or additionally, the overmould may be adapted to connect the hollow structure to the frame of the breathing mask or form such a frame. In an embodiment, the support structure comprises lugs for attaching the filled hollow structure to the frame of the breathing mask and/or to a gear, a headgear or other means for fastening such a mask to the face of a patient. The breathing mask may be a nasal breathing mask or a full face mask.

Alternatively or additionally the support structure may be provided with a handling structure adapted for handling the support structure and/or the hollow structure during manufacture. In this form, the present technology advantageously facilitates robot assisted manufacture.

According to an embodiment, the second material for overmoulding the hollow structure may be of a functional nature. In the embodiment where the hollow structure defines a cushion of a face mask, particularly for use in breathing therapy such as CPAP or VPAP™, the second material may be formed as a frame or cushion clip structure to be connected to a frame.

Another aspect of the present technology relates to a filled hollow structure produced by a method according to an embodiment of the present technology as well as to a tool for producing such filled hollow structure and/or for performing a method according to an embodiment of the present technology. The filled hollow structure comprises an open hollow structure from a first material that is at least partially closed by a closing structure and filled with a filler medium, the filled hollow structure being overmoulded with a second material. The closing structure may be positioned between an opening of the hollow structure and the overmould so as to separate the filler medium and the overmould apart. The overmould may be adapted as a functional structure.

The tool may comprise a first mould half, a second mould half and a third mould half. The first mould half is configured to form a cavity with the general shape of the negative of an open hollow structure when mating with the second mould half. This particularly allows the hollow structure or bladder to be moulded. The first mould half is further configured to hold the open hollow structure while the open hollow structure is at least partially closed with a closing structure and filled with a filler medium. The third mould half is configured to form a cavity with the general shape of the negative of an overmould when mating with the first mould half holding the filled hollow structure. The first and/or third mould is/are preferably adapted to additionally hold and include the above discussed support structure. This preferably allows the overmould to be specifically shaped on the closed and filled hollow structure. Preferably, the tool is adapted to and allows the hollow structure to remain in the first mould half during the subsequent production or method steps such as filling, closing and overmoulding.

According to another additional or alternative aspect of the present technology a tool for producing a filled hollow structure by a method according to an embodiment of the present technology comprises a first mould half, a second mould half and a third mould half. The second mould half is configured for producing an open hollow structure of a first material when being combined with the first mould half and the third mould half is configured for overmoulding the filled hollow structure when being combined with the first mould half holding the filled hollow structure. The first mould half is configured to hold the open hollow structure while the open hollow structure is at least partially closed with a closing structure and filled with a filler medium. Further aspects of the present technology, relate to methods for using said tool in order to produce a filled hollow structure.

The closing structure provided according to the method of the present technology may prevent the second material used for overmoulding the filled hollow structure from encroaching the filler medium. Furthermore, the filling of the filler material into the hollow structure may be better controlled. For example, overflow air and gaps can be avoided. While the filler material may otherwise only fill up to a horizontal 'gravity' line, the closing structure permits a non-horizontal or non-planar fill.

Thus in accordance with the present technology, the filler material may be added in an injection step as an alternative to a pouring step. An advantage of the technology is that it allows for filling of a complex three dimensional shape, for example a non-planar shape. For example a gel cushion for a full-face mask has a complex shape to effect a seal on a face in both the nasal bridge region and the chin region. The present technology enables the manufacture of a full-face gel cushion that follows the complex three dimensional shape of the face and have, in one form, a constant wall height of gel. In another form, the full face gel cushion may have a first wall height in one region of the face and a second wall height in a second region of the face. Thus more complex shapes may be manufactured.

The filled hollow structure of the present technology may, thus, be produced in a single moulding tool, obviating handling operations, positioning and/or repositioning of the hollow structure. Therefore, the process may be fully automated. Cycle times and production costs may be reduced.

Furthermore, given that the hollow structure does not have to be handled and repositioned, a cleaner look and finish of the overmoulded filled hollow structure may be achieved. Since the filler medium can be fully encapsulated or enclosed by providing the open hollow structure with the closing structure the risk of microbes or other unwanted materials getting into the cushion and contaminating it can be reduced. Further, forces acting on the bottom or transmission wall of the filled hollow structure can be distributed evenly, reducing the loads acting on joints or seams. Leaking risk may thus be minimized. Furthermore, when the filled hollow structure is attached to means for holding the structure on a patient's head via the support structure, the amount of connection elements required is reduced, minimizing production costs and the number of parts requiring disinfection. The technology also allows advantageous designs of, e.g., face masks to be established due to the integral and condensed hollow structure according to the present technology featuring multiple functionalities in one part, manufactured in one contiguous process in one tool.

According to particularly advantageous embodiments of the technology the hollow structure is filled with the filler medium after being at least partially closed by provision of the closing structure. In this case the closing structure may prevent the filler medium from overflowing, allowing, e.g., other means than gravity fill to be employed in order to fill the closed hollow structure. The hollow structure may, thus, be filled more quickly, leading to a more consistent and homogeneous fill.

The closing structure may have barcodes, branding and/or other printed information on it. The barcodes, branding and/or printed information may be internal, i.e., a person would not be able to tamper with it, as it would be enclosed e.g. by the support structure or the overmoulding.

In an alternative form, an information carrying medium may be embedded within the cushion. For example an RFID or NFC tag could be embedded within the cushion.

The present technology, therefore, overcomes at least some of the disadvantages of the prior art. In particular, the hollow structure does not have to be taken out of the mould and placed on a jig. Formation of wrinkles and the deformation of the hollow structure is, thus, effectively avoided. Since, the shape of the produced hollow structures and the volume of the filling material therein is consistent, leading to a manufacturing process that provides reliable results even on a large scale. A further advantage is that the hollow structure can be sealed from the surrounding environment during the production process completely, preventing creation of microbe traps or contamination areas.

The following aspects are preferred embodiments of the technology.

1. A method for producing a filled hollow structure, comprising:
   producing an open hollow structure from a first material;
   providing a closing structure to at least partially close the open hollow structure;
   filling the hollow structure with a filler medium; and
   overmoulding the filled hollow structure with a second material.
2. A method according to aspect 1, wherein the hollow structure is filled after at least partially closing the open hollow structure with the closing structure.
3. A method according to aspects 1 or 2, wherein providing the closing structure comprises inserting a plug into the open hollow structure.

4. A method according to aspect 3, wherein the plug snugly fits into an opening of the open hollow structure.
5. A method according to aspects 3 or 4, wherein the plug closes the open hollow structure.
6. A method according to aspects 3 to 5, wherein the plug is preformed or moulded onto the open hollow structure.
7. A method according to aspects 3 to 6, wherein the plug provides at least one filling structure, preferably an opening, for filling the open hollow structure with the filler medium and/or at least one evacuation structure, preferably an opening, for gas or fluid evacuation.
8. A method according to aspects 3 to 7, wherein the plug is provided with at least one hole for filling the open hollow structure with the filler medium and/or at least one hole for gas or fluid evacuation.
9. A method according to any one of the preceding aspects, wherein the method comprises multi-component injection moulding.
10. A method according to any one of the preceding aspects, wherein the open hollow structure is produced in a cavity of a moulding tool and remains in a mould half when being closed.
11. A method according to any one of the preceding aspects, wherein the hollow structure is produced and closed in a cavity of a moulding tool and remains in a mould half when being filled.
12. A method according to any one of the preceding aspects, wherein the hollow structure is produced, closed and filled in a cavity of a moulding tool and remains in a mould half when being overmoulded.
13. A method according to any one of the preceding aspects, wherein the first material is silicone.
14. A method according to any one of the preceding aspects, wherein the closing structure is formed of silicone.
15. A method according to any one of the preceding aspects, wherein the second material is silicone, liquid silicone rubber (LSR), thermoplastic elastomer (TPE), thermoplastic polyurethane (TPU), thermoplastic vulcanizate (TPV).
16. A method according to any one of the preceding aspects, wherein the second material comprises silicone, liquid silicone rubber (LSR), thermoplastic elastomer (TPE), thermoplastic polyurethane (TPU), thermoplastic vulcanizate (TPV) and/or the first material.
17. A method according to any one of the preceding aspects, wherein the closing structure has a hardness that is higher than the hardness of the first material and/or higher than the hardness of the second material.
18. A method according to any one of the preceding aspects, wherein the filler medium is a fluid, gas, liquid, foam, expandable fluid, powder and/or gel.
19. A method according to any of the preceding aspects, wherein the filler medium is or comprises silicone, oil, high viscosity fluids, wax, low viscosity fluids and/or low hardness elastomers.
20. A method according to any one of the preceding aspects, further comprising at least partially curing the filler medium.
21. A method according to any one of the preceding aspects, wherein the hollow structure is completely or partially filled with the filler medium.
22. A method according to any one of the preceding aspects, wherein the hollow structure comprises a connection adapted to allow a vacuum or pressure to be applied to the hollow structure.
23. A method according to aspects 1-22, wherein the tool is heated.
24. A method according to aspects 1-23, wherein the walls of the open hollow structure act as an insulating layer to prevent the filler medium from curing in the hot tool to quickly.
25. A method according to any one of the preceding aspects, further comprising providing a support structure between the filler medium and the second material.
26. A method according to any one of the preceding aspects, further comprising providing a support structure between the closing structure and the second material.
27. A method according to aspects 25 or 26, wherein the support structure substantially inhibits contact between the second material and the filler medium.
28. A method according to aspects 25-27, wherein the support structure substantially obstructs at least one opening provided in the closing structure.
29. A method according to aspects 25-28, wherein the support structure is a plastic support member, preferably a rigid plastic support member.
30. A method according to aspects 25-29, wherein the material used for the support structure is harder than the first material and/or harder than the second material and/or harder than a material used for the closing structure.
31. A method according to any one of the preceding aspects, further comprising providing the hollow structure with further structures to form a breathing mask.
32. A method according to any one of the preceding aspects, wherein the hollow structure is a cushion for a breathing mask.
33. A method according to aspects 25-32, wherein the support structure is provided with a connection structure adapted to connect the hollow structure to a further structure and/or wherein the support structure is provided with a handling structure adapted for handling the support structure and/or the hollow structure during manufacture.
34. A method according to aspect 33, wherein the connection structure is adapted to connect the hollow structure to the frame of a mask and/or to a gear or headgear of a mask assembly.
35. A method according to aspect 34, wherein the connection structure comprises lugs for attaching the filled hollow structure to the frame of a mask.
36. A method according to any one of the preceding aspects, wherein the overmoulded second material forms a frame of a mask and/or a clip for connecting the filled hollow structure to such a frame.
37. A filled hollow structure comprising
    an open hollow structure from a first material;
    wherein the open hollow structure is at least partially closed by a closing structure;
    the hollow structure is filled with a filler medium; and
    the filled hollow structure is overmoulded with a second material.
38. A tool for producing a filled structure comprising
    a first mould half;
    a second mould half; and
    a third mould half;
    wherein the second mould half is configured to form a cavity with the shape of the negative of an open hollow structure when mating with the first mould half
    the first mould half is configured for holding the open hollow structure while the open hollow structure is at least partially closed with a closing structure and filled with a filler medium; and the third mould half is configured to form a cavity with the shape of the negative of an overmould when cooperating with the first mould half holding the filled hollow structure 39. Use of the tool of aspect 38 for producing a filled hollow structure, preferably a filled hollow structure according to aspect 37, preferably using the method according to any one of aspects 1-36.

Other aspects, features, and advantages of this invention will become apparent from the following detailed description when taken in conjunction with the accompanying drawings, which are a part of this disclosure and which illustrate, by way of example, principles of the invention.

BRIEF DESCRIPTION OF THE DRAWINGS

The accompanying drawings facilitate an understanding of the various embodiments of this invention. In such drawings:

FIG. 4 is a three dimensional view of a filled hollow structure according to an embodiment of the present technology in the assembled state;

FIG. 5 is a cross-sectional view of an open hollow structure in a tool for producing the open hollow structure according to an embodiment of the present technology;

DETAILED DESCRIPTION OF ILLUSTRATED EMBODIMENTS

In this specification, the word "comprising" is to be understood in its "open" sense, that is, in the sense of "including", and thus not limited to its "closed" sense, that is the sense of "consisting of". A corresponding meaning is to be attributed to the corresponding words "comprise", "comprised" and "comprises" where they appear.

In the claims, the term "comprises/comprising" does not exclude the presence of other elements or steps. Furthermore, although individually listed, a plurality of means, elements or method steps may be implemented. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc. do not preclude a plurality.

The invention also covers all further features shown in the figures individually although they may not have been described in the afore description. Reference signs in the claims are provided merely as a clarifying example and shall not be construed as limiting the scope of the claims in any way. The present invention also covers the exact terms, features, values and ranges etc. in case these terms, features, values and ranges etc. are used in conjunction with terms such as about, around, generally, substantially, essentially, at least etc. (i.e., "about 3" shall also cover exactly 3 or "substantially inhibit" shall also cover inhibit).

The following description is provided in relation to several preferred embodiments underlying the present invention which will be discussed in a non-limiting way by reference to the Figures in the following. The embodiments may share common characteristics and features.

Figure 1:
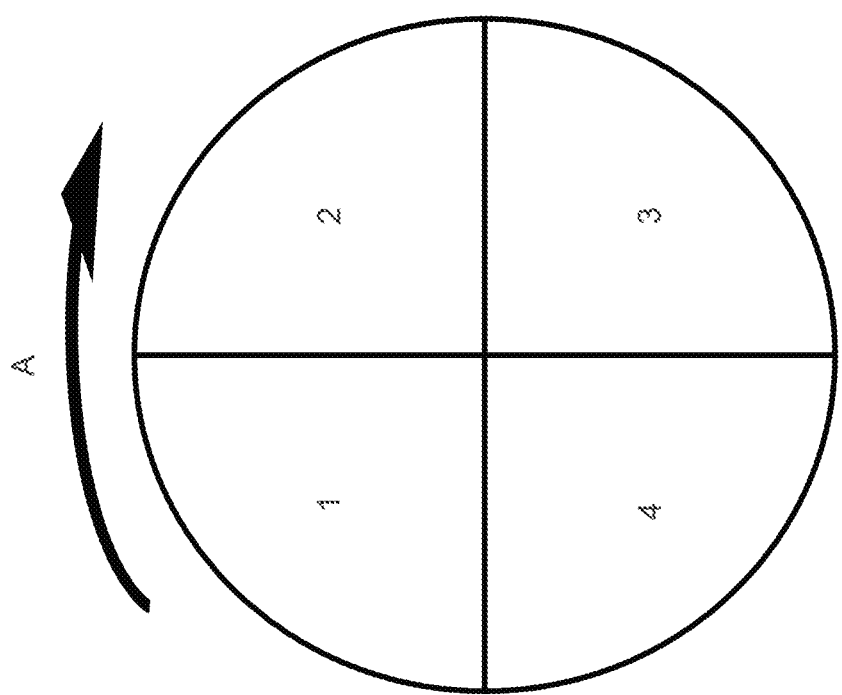
FIG. 1 is a schematic view of a production cycle according to an embodiment of a method of the present technology.

FIG. 1 is a schematic view of a method for producing a filled hollow structure according to an embodiment of the present technology. In particular, arrow A indicates the path or successive steps for producing a filled hollow structure according to an embodiment of the method of the present technology.

At each position 1 to 4, one or more method steps may be carried out according to embodiments of the present technology. In step 1, the open hollow structure or bladder may be produced by injection moulding a plastic structure having thin wall thicknesses from a first material, e.g., silicone (e.g., liquid silicone rubber) in a moulding tool having a first mould half and a second mould half. The open hollow structure may then be at least partially closed by providing a closing structure such as a plug in step 2 for then being filled with a filler medium in step 3 through a filling structure provided in the closing structure. Subsequently, and optionally, a support may be inserted. As indicated by arrow A, according to embodiments of the method the open hollow structure may be closed first (forming a closed hollow structure) and filled subsequently. The now filled hollow structure may then be overmoulded with a second material. The open hollow structure produced in step 1 may remain in the first mould half during steps 2, 3 and 4. The closed filled and overmoulded hollow structure may be taken out or ejected from the moulding tool after being overmoulded in step 4.

Figure 2:
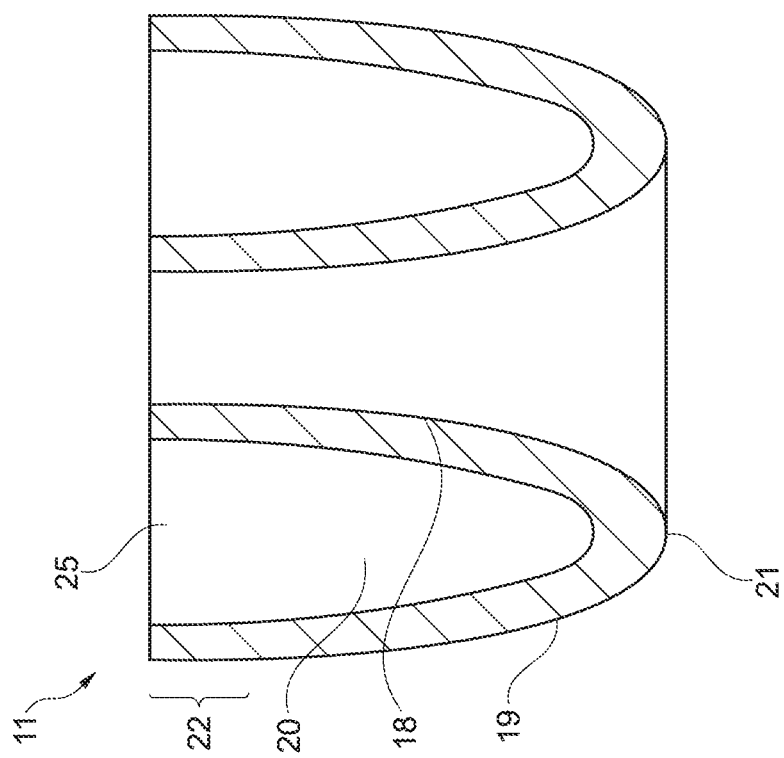
FIG. 2 is a cross-sectional view of an open hollow structure according to an embodiment of the present technology.

FIG. 2 illustrates an open hollow structure 11. As illustrated, open hollow structure 11 in an embodiment includes a thin inner wall 18 and a thin outer wall 19 wherein a hollow or hollow area 20, such as a pocket or a cavity, is formed between inner wall 18 and outer wall 19. Inner wall 18 and outer wall 19 merge at one end of the structure via a bottom or transition wall 21. Hollow structure 11 may include a closing or sealing area 22, preferably at a side opposite transition wall 21, that defines an opening 25 in which the hollow area 20 is open to the environment. In the illustrated embodiment, opening 25 is a slot extending around the perimeter of the open hollow structure between the inner wall 18 and the outer wall 19. According to an embodiment, the hollow structure may have a form and/or configuration of face masks for delivering breathable gas or fluid to a patient and/or of hollow cushions of such masks, e.g., a basically triangular shape when seen from above. Depending on the respective application, hollow structure 11 may comprise different wall thicknesses as well as various changes in geometry depending on the individual requirements of the desired use.

Figure 3:
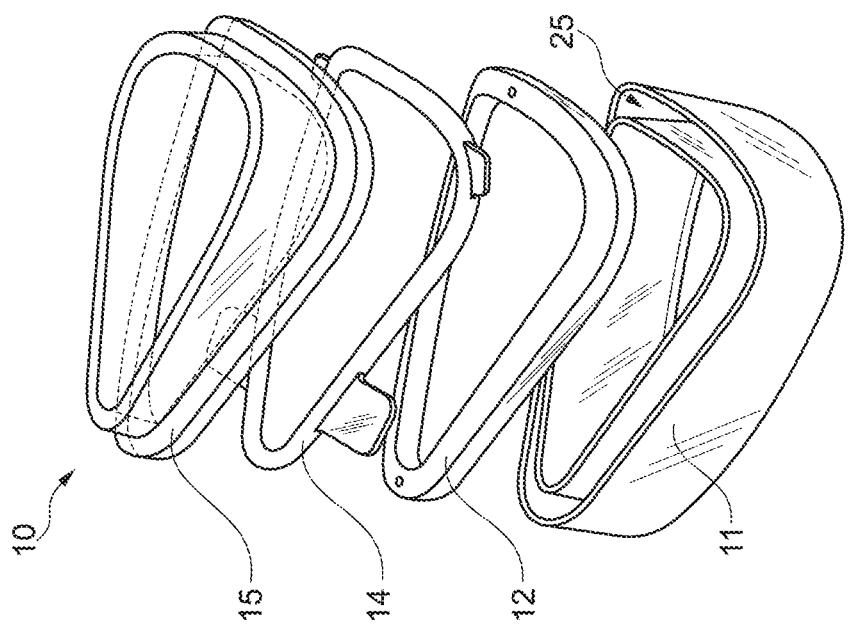
FIG. 3 is a three dimensional exploded view of a filled hollow structure according to an embodiment of the present technology.

FIG. 3 illustrates components of a filled hollow structure 10 according to an embodiment of the present technology. The filled hollow structure 10 comprises an open hollow structure 11, here in the shape of a cushion 3100 of a breathing mask 3000, a closing structure 12, and an overmould 15. Optionally, a support structure 14 may be provided.

As shown in FIG. 3, closing structure 12 may be a plug that closes the opening 25 when inserted into closing area 22 of the open hollow structure 11. Closing structure 12 may snugly or sealingly fit into opening 25. According to an embodiment, closing structure 12 may have substantially the same shape as the hollow structure 11 when viewed from above.

As further shown in FIG. 3, overmould 15 may generally follow the contour of the open hollow structure and/or the contour of the closing structure. For example, overmould 15 may have substantially the same shape as the hollow structure and/or the closing structure when viewed from above. According to an embodiment, the overmould may have the form and/or configuration of the frame of a mask for delivering breathable gas or fluid to a patient. According to an embodiment, the overmould may have the form and/or configuration of a clip for connecting hollow cushions of such masks to a respective frame.

FIG. 4 shows the filled hollow structure 10 according to an embodiment of the present technology in an assembled state. The support structure 14 may include lugs 28, 29 for connecting the filled hollow structure to other structures in order to form a breathing mask 3000 or to elements for supporting such a mask on a patient's face. For example, lugs 28, 29 may be adapted for connecting the filled hollow structure 10 to means for fastening a breathing mask 3000 to the face of a patient, e.g. a gear or a headgear, an attachment of a forehead support, a frame, or a tube connector. Lugs 28, 29 may also be used in order to handle the support structure and/or the filled hollow structure during manufacturing.

FIG. 5 illustrates the moulding tool 30 during step 1 of FIG. 1 in which the open hollow structure 11 is moulded in a cavity of the tool formed by the first mould half 31 when mating with the second mould half 32. In this context it should be noted that each of the mould halves may comprise several parts, inlays, cores, or ejectors pins (not shown), etc. Tool 30 may also comprise ducts and nozzles or channels adapted to apply a vacuum and/or compressed gas or fluid for use in holding hollow structure 10 on the tool 30 and/or releasing or removing hollow structure 11 or filled hollow structure 10 from the tool 30.

Figure 6:
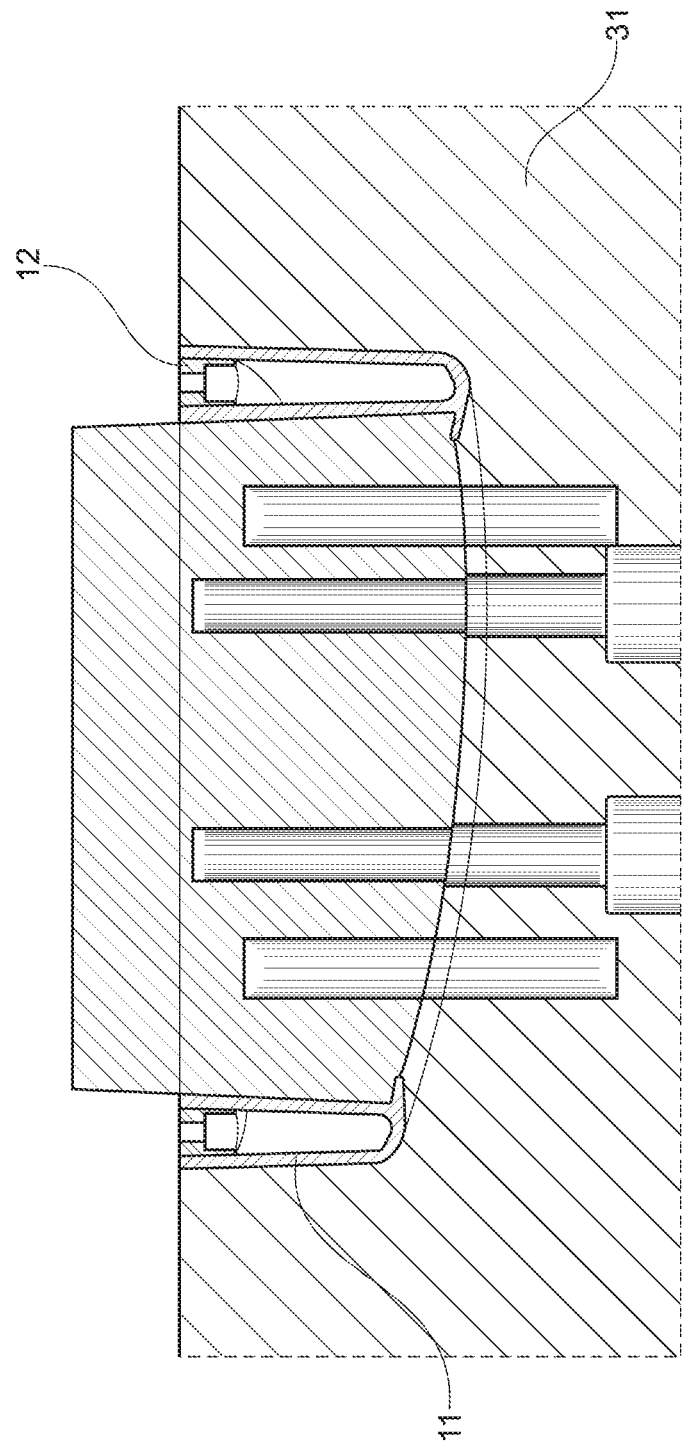
FIG. 6 is a cross-sectional view of a closed open hollow structure in a mould half of a moulding tool for producing said open hollow structure, wherein the open hollow structure has been closed with a closing structure according to an embodiment of the present technology and is set up for filling.

FIG. 6 illustrates step 2 of FIG. 1 wherein the open hollow structure 11 has been moulded and closing structure 12 has been inserted into the open hollow structure 11. Preferably, closing structure 12 is a preformed plug. However, alternatively or additionally, the closing structure or plug may also be moulded onto and/or into the open hollow structure. Closing structure 12 may be a stiff element or rather flexible and can be made, e.g., from silicone. The closing structure 12 may snugly and sealingly fit into the opening 25 and cooperate with sealing area 22 of the open hollow structure to provide a sealing closure along the perimeter of closing structure 12. As described above, open hollow structure 11 may remain in the first mould half 31 during insertion of the closing structure.

According to the present technology the hollow structure may be filled after closing the open hollow structure with the closing structure. This is, the open hollow structure may be first closed and/or sealed with the closing structure, as discussed above, and subsequently at least partially filled with a filler medium. Therefore, when a plug is used as a closing structure, the plug may provide at least one filling structure, such as a membrane or opening for filling the open hollow structure with the filler medium and/or at least one evacuation structure, such as a self closing membrane or opening for gas or fluid evacuation. E.g. the plug may be provided with at least one hole for filling the open hollow structure with the filler medium and/or at least one hole for gas or fluid evacuation.

Figure 7:
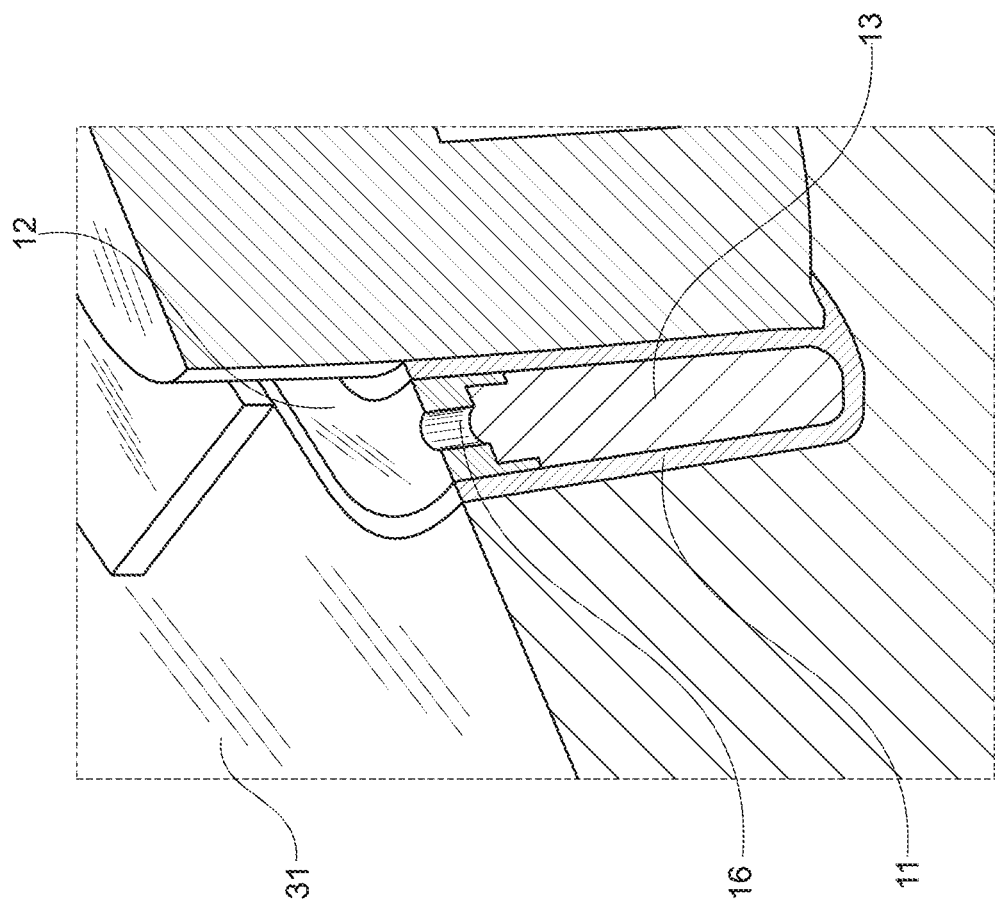
FIG. 7 is a cross-sectional view of a three dimensional detail of a closed open hollow structure set up for filling in a mould half of a moulding tool for producing said open hollow structure according to an embodiment of the present technology.

FIG. 7 shows the hollow structure 11 provided with a closing structure 12 with openings or holes 16 set up for filling. Preferably, closing structure 12 comprises at least one hole 16 for filling the hollow area 20 of the hollow structure 11 with the filler medium 13, e.g., via a nozzle. According to an embodiment, more than one filler nozzle may be used. Furthermore, closing structure 12 may comprise at least one hole 16 for evacuating gas or fluid during filling of the filler medium. The openings or holes 16 may be provided at circumferentially opposite sides of the closing structure 12. As described above, hollow structure 11 may remain in the first mould half 31 during filling with the filler medium 13.

In one form the closing structure 12 has an approximately constant cross-section around its length. In another form, the closing structure 12 has a first cross-section in a first region, and a second cross-section in a second region. In one form the first cross-section and the second cross-section are different.

In an embodiment, e.g., when the filler medium is a gel or a silicone gel, the gel may be inserted cold or at room temperature as a liquid and may be subsequently heated to cure. According to a further embodiment, the gel may be inserted into the hollow area 20 preheated. This arrangement allows a faster cure. According to another embodiment, the gel may be inserted pre-cooled into the hollow area 20. This arrangement slows down the curing process, e.g., if the gel is curing too fast. The gel may be allowed to only cure partially to achieve desired properties of the structure. According to an embodiment, mould half 31 may be adapted to assist curing of the filler medium. For example, first mould half 31 may be heatable and/or coolable to allow the filler medium 13 filled into hollow area 20 to cure. Additionally, the inner wall 18 and/or the outer wall 19 of hollow structure 11 may be adapted in order to regulate how quickly the filler medium 13 is cured. The filler medium 13 may be cured by radiation, e.g., after removing the hollow structure from the mould. When a TPE is used as the filler medium 13 or comprised in the filler medium 13, it may be injected at a high temperature into a cold tool.

As a further step, preceding the filling of the hollow area 20 with a filler medium 13, a vacuum may be applied to the hollow area 20 in order to suck gas or fluid out of the hollow area 20 before the filler medium, such as a gel, is inserted. Preferably, the vacuum is controlled so as to not deform the bladder.

Figure 8:
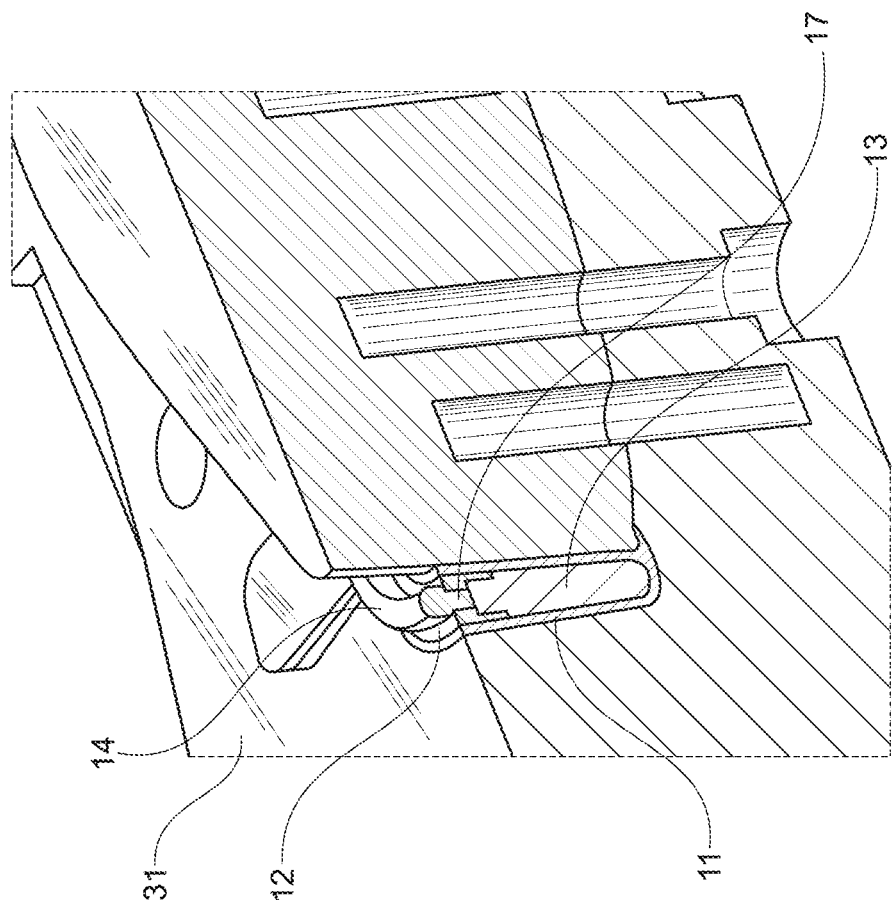
FIG. 8 is a cross-sectional view of a closed and filled open hollow structure in a mould half of a moulding tool for producing said open hollow structure, wherein the closed and filled open hollow structure has been provided with a support structure according to an embodiment of the present technology.

As shown in FIG. 8, hollow structure 11 may optionally be provided with support structure 14. Preferably, support structure 14 is provided after closing and filling hollow structure 11. In the illustrated embodiment, the support structure 14 comprises protrusions 17. As illustrated, protrusions 17 may be adapted for being inserted into and for closing holes 16 of closing structure 12. Hollow structure 11 may remain in mould half 31 while support structure 14 is provided.

Figure 9:
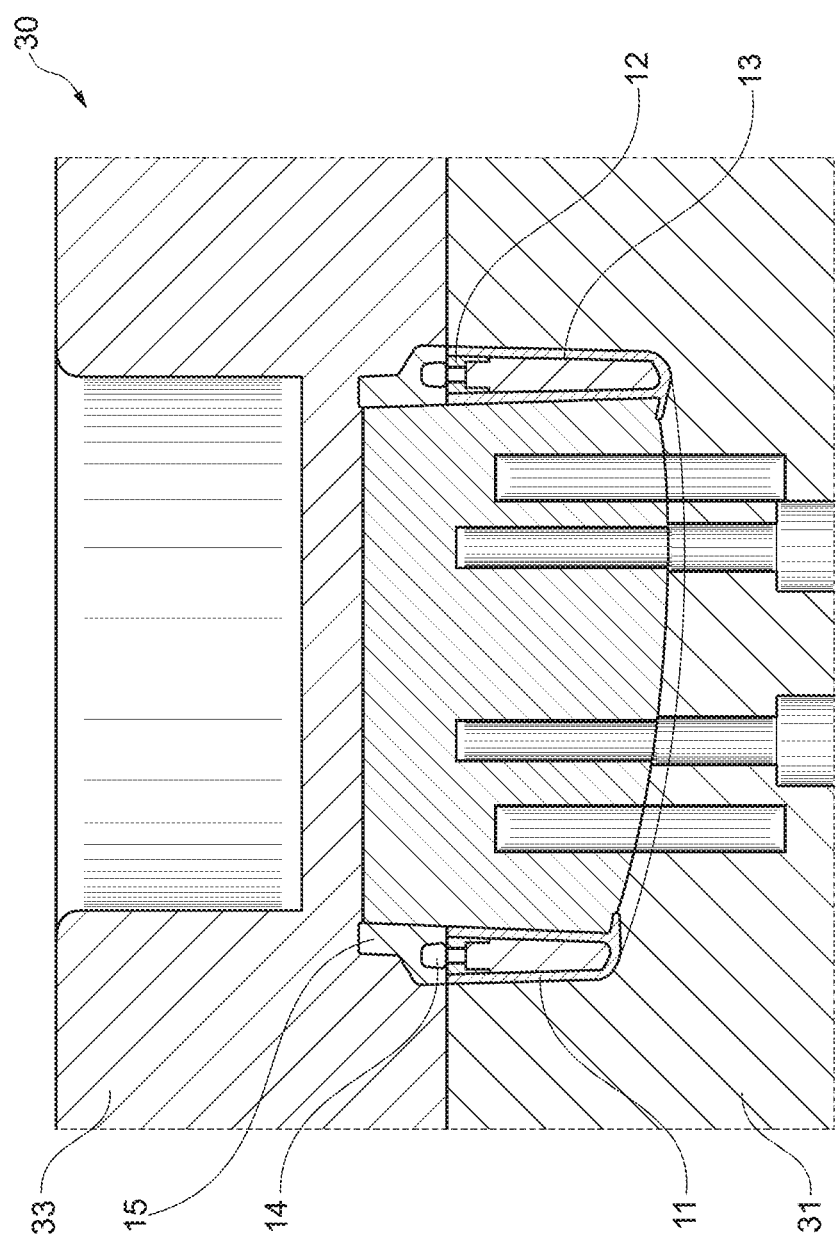
FIG. 9 is a cross-sectional view of a closed, filled and overmoulded open hollow structure in a mould half of a moulding tool for producing said open hollow structure according to an embodiment of the present technology.
Figure 10:
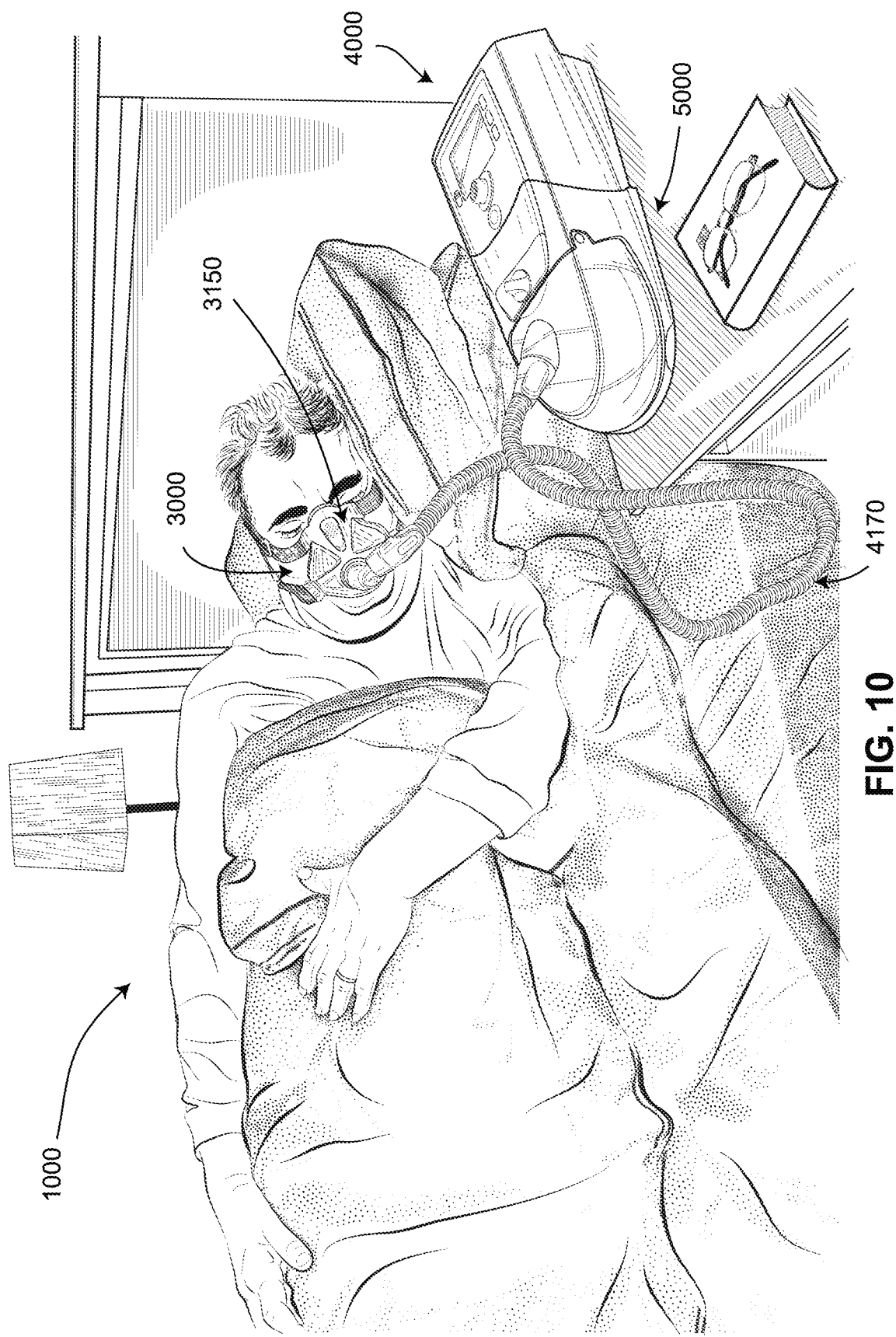
FIG. 10 is a view of a full-face breathing mask 3000 in accordance with the present technology that is connected to a PAP device 4000 and humidifier 5000 via an air delivery tube 4170 to provide positive air pressure therapy to a patient 1000.
Figure 11:
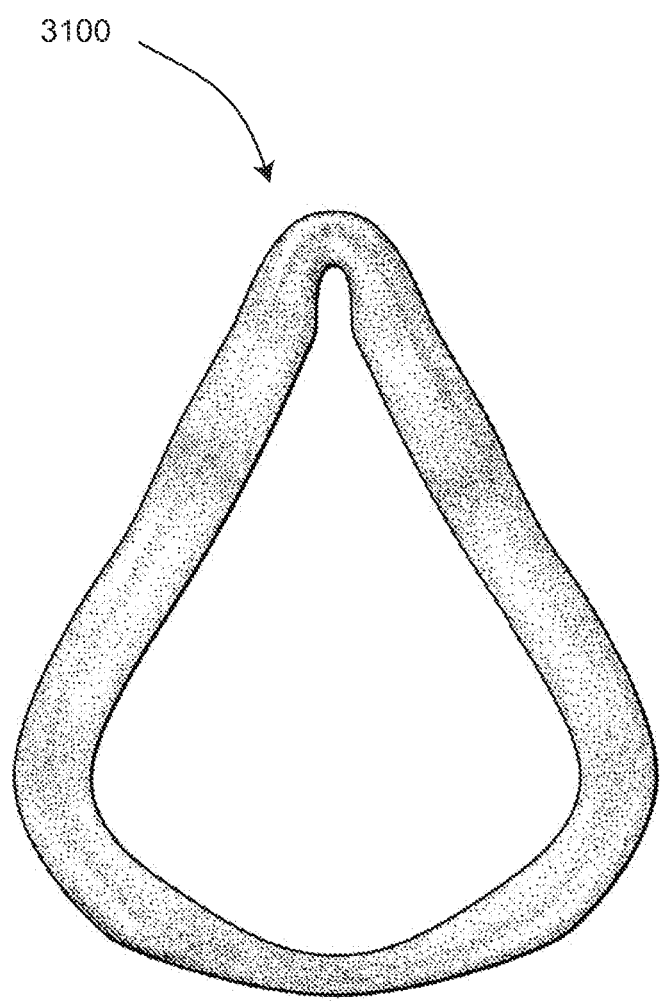
FIG. 11 shows a patient-side plan view of a cushion 3100 in accordance with one form of the present technology.

FIG. 9 shows step 4 of FIG. 1 in which the open hollow structure 11 is provided with an overmould 15 of a second material in a cavity of the tool 30 formed by the second third mould half 33 when mating with the first mould half 31 holding the filled and closed hollow structure 11. Third mould half 33 may comprise ducts and nozzles or channels adapted to apply a vacuum and/or compressed gas or fluid for use in holding hollow structure 10 on the tool 30 and/or releasing or removing hollow structure 10 from the tool 30. Furthermore, third mould half 33 may comprise ejector pins (not shown).

It should be appreciated that the above description as well as the figures relate to an exemplary embodiment of a method and product according to an embodiment of the present technology. However, the respective method as well as the product and tool and, in particular, their geometry should not be considered as being restricted by the above example. According to further embodiments, a hollow structure may not have a substantially triangular form when viewed from the top and/or bottom. For example, a hollow structure may have a substantially circular form. However, the hollow structure may also comprise further symmetrical and non-symmetrical forms in top and/or bottom views such as a rectangular, elliptical, round, ring-shaped and/or linear, etc.

As discussed above, the filler medium may be a fluid such as a gaseous and/or liquid medium, a gel, a powder, beats or pellets, foam or a foamable medium, etc. In an embodiment, the filler medium may be structured to allow the hollow structure to yield or react resiliently upon application of external pressure and provide a soft and comfortable deformable appearance. The softness or hardness of the filler medium or the filled hollow structure may be adapted according to the requirements of the desired use either during production of the filled hollow structure or after production and prior to use. This may be established by either adjusting the geometry and wall thicknesses of the hollow structure to adjust the general support of the filler medium, adjusting the degree up to which the hollow area is filled with the filler medium, adjusting the filler medium itself, as well as a combination of these factors. For example, the hollow structure may comprise different wall thicknesses and/or structures for fulfilling additional objects and/or the like.

In an embodiment, the hollow structure comprises a connection that allows a vacuum to be applied to the hollow area, thereby allowing the vacuum to deform the hollow structure so that a desired shape may be achieved and maintaining the vacuum in the hollow area after closure of the respective connection so that the shape of the hollow structure may be maintained. Further, a desired shape or individual shape may be formed and fixed by, e.g., a curing process of the filler medium. In an embodiment, the filler medium and thus the filled hollow structure may still be deformable and soft to a certain degree even after fixation of a desired shape as discussed above. For example, the hollow structure as well as the filling may be at least partially flexible and/or may be brought into a flexible condition.

In an embodiment, the hollow structure may be made of a silicone material, e.g., liquid silicone rubber, and the filler medium may also be made of a silicone material, e.g., liquid silicone rubber, in a substantially liquid aggregate state (e.g., such as gel) which may be achieved by partial curing or adding additives. In an embodiment, the overmould may be made of silicone material, e.g., liquid silicone rubber.

Figure 12A:
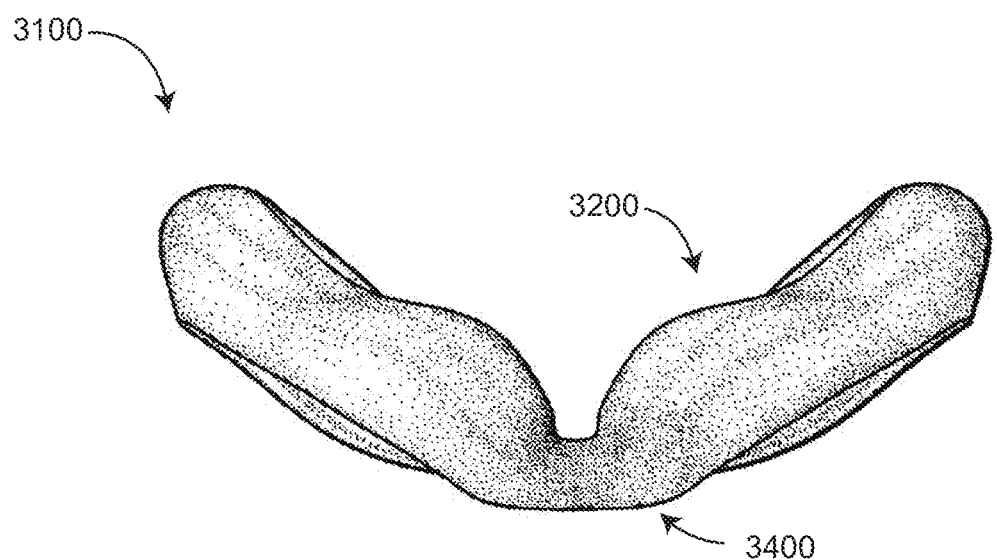
FIG. 12a shows a nasal-bridge end elevation view of a cushion 3100 in accordance with one form of the present technology illustrating a patient side 3200 of the cushion and a non-patient side 3400 of the cushion 3100.
Figure 12B:
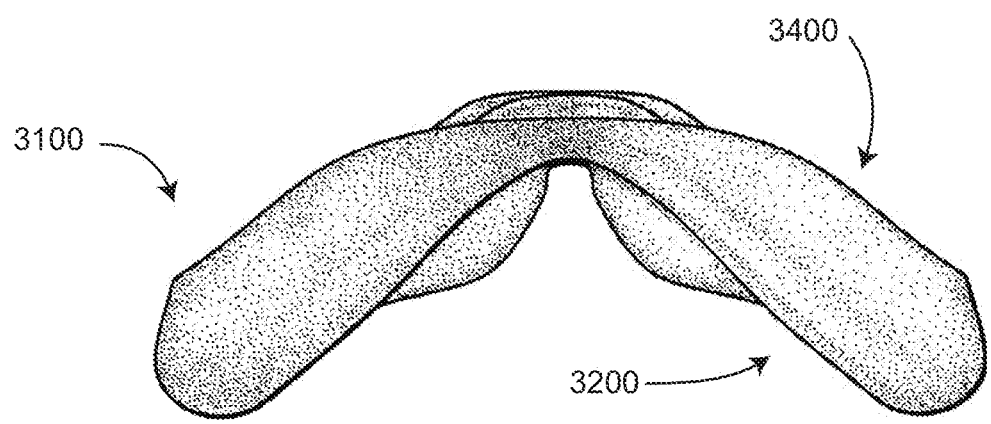
FIG. 12b shows a chin end elevation view of a cushion 3100 in accordance with one form of the present technology illustrating a patient side 3200 of the cushion and a non-patient side 3400 of the cushion 3100.
Figure 13:
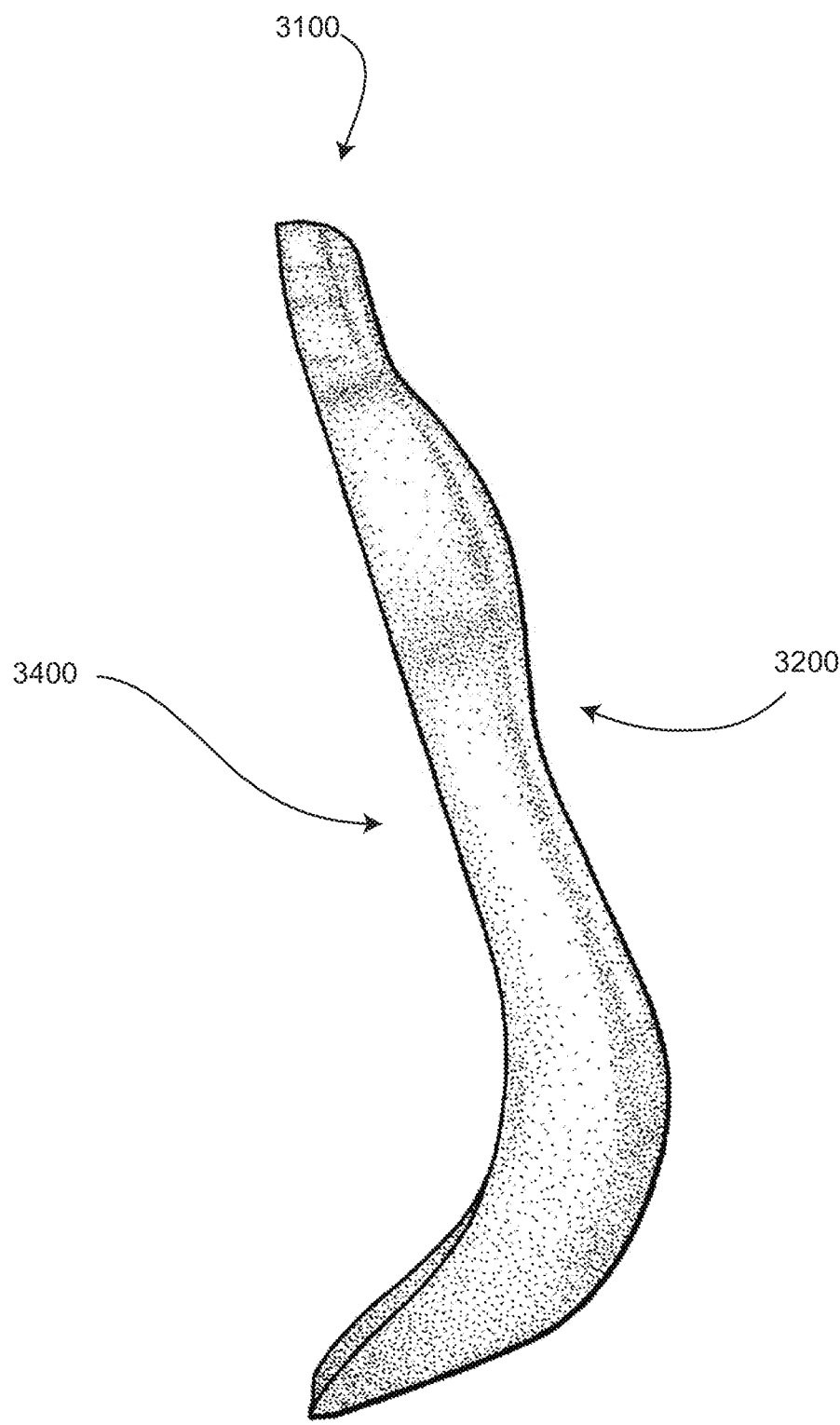
FIG. 13 shows a side elevation view of a cushion 3100 in accordance with one form of the present technology illustrating a patient side 3200 of the cushion and a non-patient side 3400 of the cushion 3100.
Figure 14:
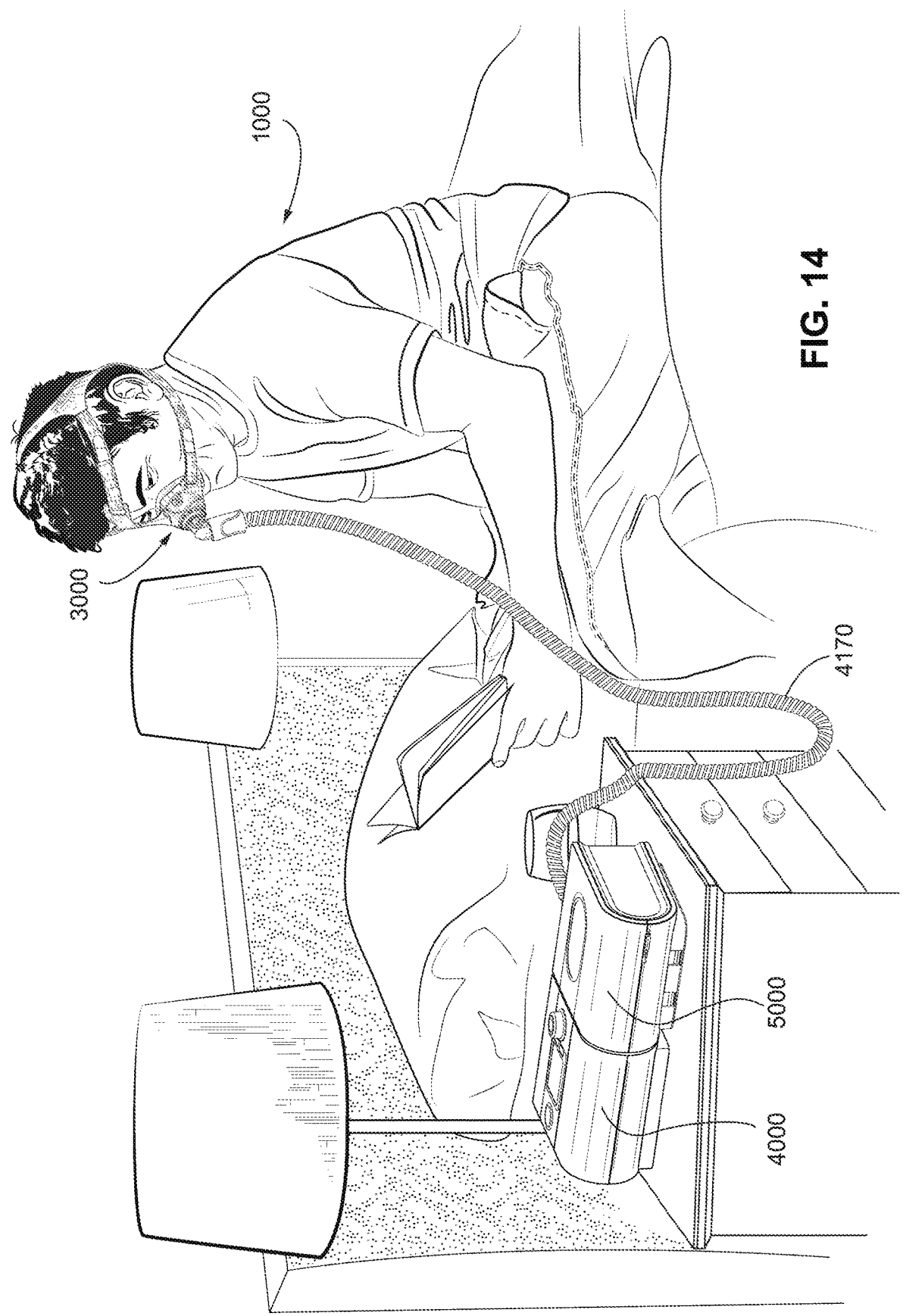
FIG. 14 shows a nasal breathing mask 3000 in accordance with one form of the present technology. Also shown is a PAP device 4000, a humidifier 5000 and an air delivery conduit 4170.

In one form of the present technology a breathing mask 3000 comprises a cushion 3100 that is connected to a Positive Airway Pressure (PAP) device 4000 and humidifier 5000 via an air delivery tube 4170. In one form of the present technology CPAP therapy may be delivered to a patient 1000. In another form, other forms of respiratory therapy may be delivered to a person. In one form the breathing mask 3000 comprises a cushion 3100, and a frame 3150 to which the cushion 3100 is connected. In one form the frame 3150 defines part of a plenum chamber. The cushion 3100 has a patient side 3200 which is constructed and arranged to contact a region of a patient's face in use. The cushion 3100 has a frame side 3400 that is constructed and arranged to contact a frame 3150 in use. Preferably the frame side 3400 of the cushion is non-planar. See FIGS. 12a, 12b and 13.

An advantage of the present technology is that it avoids the need for using a welding process, such as ultrasonic welding. However, an ultrasonic welding process may be used if desired.

In an alternative form of the present technology, the over moulding step is not included, and the combination of filled channel and cap is located in a clamp, frame or other protective structure.

One advantage of the present technology is that a number of steps may be run in parallel. For example, while one assembly is being over-moulded, one hollow structure may be filled, another may be closed, and a further hollow structure may be being moulded. This may reduce cycle time, and lead to higher output.

Another advantage of the present technology is that an open channel may be created around the entire perimeter of the cushion. Thus, for example, the whole perimeter may be filled with gel.

Another advantage of the present technology is that it simplifies the process for having different amounts of filler medium in different portions of the hollow structure. For example, when the closing structure has first- and second-crosssections in different regions, the corresponding complementary amount of filler medium may be different in those different regions.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

| Table of Part and Step references | |
|---|---|
| Part or step | Reference |
| Moulding open hollow structure | 1 |
| Closing open hollow structure | 2 |
| Filling closed hollow structure | 3 |
| Overmoulding | 4 |
| Filled hollow structure | 10 |
| Open hollow structure | 11 |
| Closing structure | 12 |
| Filler medium | 13 |
| Support structure | 14 |
| Overmould | 15 |
| Openings or holes | 16 |
| Protrusions | 17 |
| Inner wall | 18 |
| Outer wall | 19 |
| Hollow area | 20 |
| Transition wall | 21 |
| Closing area | 22 |
| Opening | 25 |
| Lug | 28 |
| Lug | 29 |
| Tool | 30 |
| First mould half | 31 |
| Second mould half | 32 |
| Third mould half | 33 |
| Patient | 1000 |
| Breathing mask | 3000 |
| Cushion | 3100 |
| Frame | 3150 |
| Patient side | 3200 |
| Frame side | 3400 |
| PAP device | 4000 |
| Air delivery tube | 4170 |
| Humidifier | 5000 |

What is claimed is:

1. A filled hollow structure, comprising:
a hollow structure comprising a first material and having an opening formed therein;
a closing structure to at least partially close the opening in the hollow structure;
a filler medium provided in the hollow structure to fill the hollow structure; and
a second material overmoulded onto the hollow structure filled with the filler medium,
wherein the closing structure has a hardness that is higher than the hardness of the first material and/or higher than the hardness of the second material,
wherein the closing structure is a plug having a side wall surface that directly engages a side wall surface of the hollow structure, and
wherein the plug has a central portion with a first height and the side wall surface of the plug has a second height greater than the first height.

2. A filled hollow structure, comprising:
a hollow structure comprising a first material and having an opening formed therein;
a closing structure to at least partially close the opening in the hollow structure;
a filler medium provided in the hollow structure to fill the hollow structure; and
a second material overmoulded onto the hollow structure filled with the filler medium,
wherein the closing structure has a hardness that is higher than the hardness of the first material and higher than the hardness of the second material.

3. The filled hollow structure according to claim 2, wherein the hollow structure has a patient side seal which is constructed and arranged to contact a region of a patient's face in use.

4. The filled hollow structure according to claim 3, wherein the hollow structure defines a patient opening to receive at least part of the patient's nose in use, and the seal extends inwards towards the patient opening.

5. The filled hollow structure according to claim 2, wherein the hollow structure when filled with the filler medium is deformable.

6. The filled hollow structure according to claim 2, wherein the closing structure is a plug having a side wall surface that directly engages a side wall surface of the hollow structure.

7. The filled hollow structure according to claim 6, wherein the opening extends parallel to the side wall surface of the plug and the side wall surface of the hollow structure.

8. The filled hollow structure according to claim 6, wherein the plug has a central portion with a first height and the side wall surface of the plug has a second height greater than the first height.

9. The filled hollow structure according to claim 6, wherein the plug directly engages the side wall surface of the hollow structure.

10. The filled hollow structure according to claim 6, wherein the plug provides at least one filling structure, including an opening, for filling the open hollow structure with the filler medium and/or for evacuating the filler medium from the hollow structure.

11. The filled hollow structure according to claim 2, wherein the first material is silicone.

12. The filled hollow structure according to claim 11, wherein the closing structure is formed of silicone.

13. The filled hollow structure according to claim 2, wherein the second material is silicone, liquid silicone rubber (LSR), thermoplastic elastomer (TPE), thermoplastic polyurethane (TPU), and/or thermoplastic vulcanizate (TPV).

14. The filled hollow structure according to claim 2, wherein the second material comprises silicone, liquid silicone rubber (LSR), thermoplastic elastomer (TPE), thermoplastic polyurethane (TPU), thermoplastic vulcanizate (TPV) and/or the first material.

15. The filled hollow structure according to claim 2, wherein the filler medium is a fluid, gas, liquid, foam, expandable fluid, powder and/or gel.

16. The filled hollow structure according to claim 2, wherein the hollow structure is completely or partially filled with the filler medium.

17. The filled hollow structure according to claim 2, further comprising a support structure provided between the filler medium and the second material, the support structure including lugs adapted to attach the filled hollow structure to a frame of a respiratory mask.

\* \* \* \* \*